(12) United States Patent
Iyengar (10) Patent No.: US 10,831,994 B2
(45) Date of Patent: Nov. 10, 2020

(54) NAMING CONVENTION RECONCILER

(71) Applicant: INTERNATIONAL BUSINESS MACHINES CORPORATION, Armonk, NY (US)

(72) Inventor: Arun K. Iyengar, Yorktown Heights, NY (US)

(73) Assignee: International Business Machines Corporation, Armonk, NY (US)

(*) Notice: Subject to any disclaimer, the term of this patent is extended or adjusted under 35 U.S.C. 154(b) by 78 days.

(21) Appl. No.: 15/854,115

(22) Filed: Dec. 26, 2017

(65) Prior Publication Data

US 2019/0197113 A1 Jun. 27, 2019

(51) Int. Cl.
| | | |
|---|---|---|
| *G06F 40/247* | (2020.01) | |
| *G06F 16/2458* | (2019.01) | |
| *G16H 50/70* | (2018.01) | |
| *G06F 16/36* | (2019.01) | |
| *G06F 40/205* | (2020.01) | |
| *G06F 40/242* | (2020.01) | |
| *G06F 16/22* | (2019.01) | |

(52) U.S. Cl.
CPC ........ *G06F 40/247* (2020.01); *G06F 16/2462* (2019.01); *G06F 16/367* (2019.01); *G06F 40/205* (2020.01); *G06F 40/242* (2020.01); *G16H 50/70* (2018.01); *G06F 16/2255* (2019.01)

(58) Field of Classification Search
USPC .......................................... 704/1, 7–10, 257
See application file for complete search history.

(56) References Cited

U.S. PATENT DOCUMENTS

| | | | | |
|---|---|---|---|---|
| 9,275,339 | B2* | 3/2016 | Culbertson | G06N 7/005 |
| 10,157,348 | B2* | 12/2018 | Ishiguro | G06N 20/00 |
| 2010/0110455 | A1* | 5/2010 | Woolfe | G01J 3/46 |
| | | | | 358/1.9 |
| 2013/0283398 | A1* | 10/2013 | Wu | G06F 21/60 |
| | | | | 726/28 |
| 2014/0355747 | A1* | 12/2014 | Kobayashi | H04M 3/42042 |
| | | | | 379/142.06 |

(Continued)

OTHER PUBLICATIONS

Leaman et al. DNorm: disease name normalization with pairwise learning to rank; Bioinformatics, vol. 29; Nov. 15, 2013.*

(Continued)

*Primary Examiner* — Leonard Saint Cyr
(74) *Attorney, Agent, or Firm* — Reza Sarbakhsh (57) ABSTRACT

Embodiments of the present invention disclose a method, a computer program product, and a computer system for a naming convention reconciler. A computer receives and pre-processing first dictionary 114 and second dictionary 116. In addition, the computer parses the pre-processed dictionaries to extract one or more names from each of the two dictionaries. The computer then generates a hash table of the names extracted from the second dictionary and searches the hash table for names that include a word in common with a name extracted from first dictionary 114. Based on identifying a name in the hash table that includes a word in common with a name extracted from first dictionary 114, the computer determines a similarity between the names and stores an association between the names having a greatest similarity.

17 Claims, 7 Drawing Sheets

(56) References Cited

U.S. PATENT DOCUMENTS

2015/0356173 A1* 12/2015 Aikawa .............. G01C 21/3611
                                                      707/722
2018/0039645 A1*  2/2018 Simak ................... G06Q 10/06
2018/0349805 A1* 12/2018 Simak ................... G06Q 10/06

OTHER PUBLICATIONS

Wikipedia, "Category: String similarity measures," https://en.wikipedia.org/wiki/Category:String_similarity_measures, Printed on Oct. 12, 2017, pp. 1-2.

Mell et al., "The NIST Definition of Cloud Computing," National Institute of Standards and Technology, U.S. Department of Commerce, Special Publication 800-145, Sep. 2011, pp. 1-7.

* cited by examiner

NAMING CONVENTION RECONCILER

BACKGROUND

The present invention relates to data analytics, and more particularly to reconciling synonyms between data implementing different naming conventions.

Data analysis improves with data set size, yielding results with increased insights and accuracy. However, gathering the large amounts of data needed for meaningful analysis is difficult when data is stored in accordance with different naming conventions. Many fields implement different naming conventions, some for reason of standard, location, preference, etc. For example, the domain of disease names alone includes various ontologies such as the Unified Medical Language System (UMLS), the Online Mendelian Inheritance in Man (OMIM), the International Classification of Diseases (ICD-9), the Systemized Nomenclature of Medicine (SNOMED), the National Cancer Institute (NCI) Disease Codes, and the Disease Ontology. When data is stored in accordance with different naming conventions, use of the data can prove difficult.

SUMMARY

Embodiments of the present invention disclose a method, a computer program product, and a computer system for converting a name n1 from a first naming convention to a second naming convention. In accordance with an embodiment of the method, a computer searches for at least one name from the second naming convention having a word in common with name n1 and, in response to finding a name n2 from the second naming convention having a word in common with name n1, using a metric to determine if a difference between name n1 and name n2 exceeds a threshold.

According to one embodiment of the method, the metric comprises Levenshtein distances.

In some embodiments, the method may further comprise using a metric to determine differences between name n1 and a plurality of names from the second naming convention having a word in common with name n1, and selecting a name from the plurality of names from the second naming convention having a word in common with name n1 with a minimum difference from name n1.

Moreover, in further embodiments, searching for at least one name from the second naming convention having a word in common with name n1 further comprises maintaining a hash table indexed by words, wherein a hash bucket of the hash table includes a list of identifiers of names in the second naming convention which include a word indexing the bucket of the hash table, and searching the hash table for data associated with a word included in name n1.

In yet further embodiments, the method may comprise decreasing said threshold to obtain more precise conversions between the first naming convention and the second naming convention. Conversely, the method may further comprise increasing said threshold to obtain more conversions between the first naming convention and the second naming convention.

Embodiments of the present invention further comprise a computer program product for converting a name n1 from a first naming convention to a second naming convention. In one embodiment, the computer program product includes one or more computer-readable storage devices and program instructions stored on at least one of the one or more tangible storage devices.

Moreover, in one embodiment, the program instructions comprise program instructions to search for at least one name from the second naming convention having a word in common with name n1 and, in response to finding a name n2 from the second naming convention having a word in common with name n1, using a metric to determine if a difference between name n1 and name n2 exceeds a threshold.

In some embodiments of the computer program product, the metric comprises Levenshtein distances.

In further embodiments, the computer program product may further comprise program instructions to use a metric to determine differences between name n1 and a plurality of names from the second naming convention having a word in common with name n1, and program instructions to select a name from the plurality of names from the second naming convention having a word in common with name n1 with a minimum difference from name n1.

In yet further embodiments, program instructions to search for at least one name from the second naming convention having a word in common with name n1 further comprises program instructions to maintain a hash table indexed by words, wherein a hash bucket of the hash table includes a list of identifiers of names in the second naming convention which include a word indexing the bucket of the hash table, and program instructions to search the hash table for data associated with a word included in name n1.

According to some embodiments, the computer program product may further comprise program instructions to decrease said threshold to obtain more precise conversions between the first naming convention and the second naming convention, as well as program instructions to increase said threshold to obtain more conversions between the first naming convention and the second naming convention.

Embodiments of the present invention further disclose a system for converting a name n1 from a first naming convention to a second naming convention. In some embodiments, the computer system comprises one or more processors, one or more computer-readable memories, one or more computer-readable tangible storage devices, and program instructions stored on at least one of the one or more storage devices for execution by at least one of the one or more processors via at least one of the one or more memories.

According to an embodiment of the computer system, the program instructions comprise program instructions to search for at least one name from the second naming convention having a word in common with name n1 and, in response to finding a name n2 from the second naming convention having a word in common with name n1, program instructions to apply a filter to name n1 and name n2. Moreover, if name n1 and name n2 pass the filter, the computer system includes program instructions to use a metric to determine if a difference between name n1 and name n2 exceeds a threshold.

In some embodiments of the computer system, name n1 and name n2 pass the filter if the difference in their lengths falls below a length threshold. In other embodiments, the filter is based on a quotient of a length of name n1 and a length of name n2. In addition, according to some embodiments of the system, the metric comprises a Levenshtien distance.

In yet further embodiments, the computer system further comprises program instructions to use a metric to determine differences between name n1 and a plurality of names from the second naming convention having a word in common with name n1, and program instructions to select a name from the plurality of names from the second naming convention having a word in common with name n1 with a minimum difference from name n1.

In some embodiments of the computer system, program instructions to search for at least one name from the second naming convention having a word in common with name n1 further comprises program instructions to maintain a hash table indexed by words, wherein a hash bucket of the hash table includes a list of identifiers of names in the second naming convention which include a word indexing the bucket of the hash table, and program instructions to search the hash table for data associated with a word included in name n1.

The computer system may further comprise one of program instructions to decrease said threshold to obtain more precise conversions between the first naming convention and the second naming convention, as well as program instructions to increase said threshold to obtain more conversions between the first naming convention and the second naming convention.

In some embodiments, name n1 and name n2 pass the filter if the quotient of a length of name n1 and a length of name n2 differs from 1 by less than a threshold.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Detailed embodiments of the claimed methods, computer program products, and systems are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is rather focused on the distinctive features or elements of various embodiments of the present invention.

Figure 1:
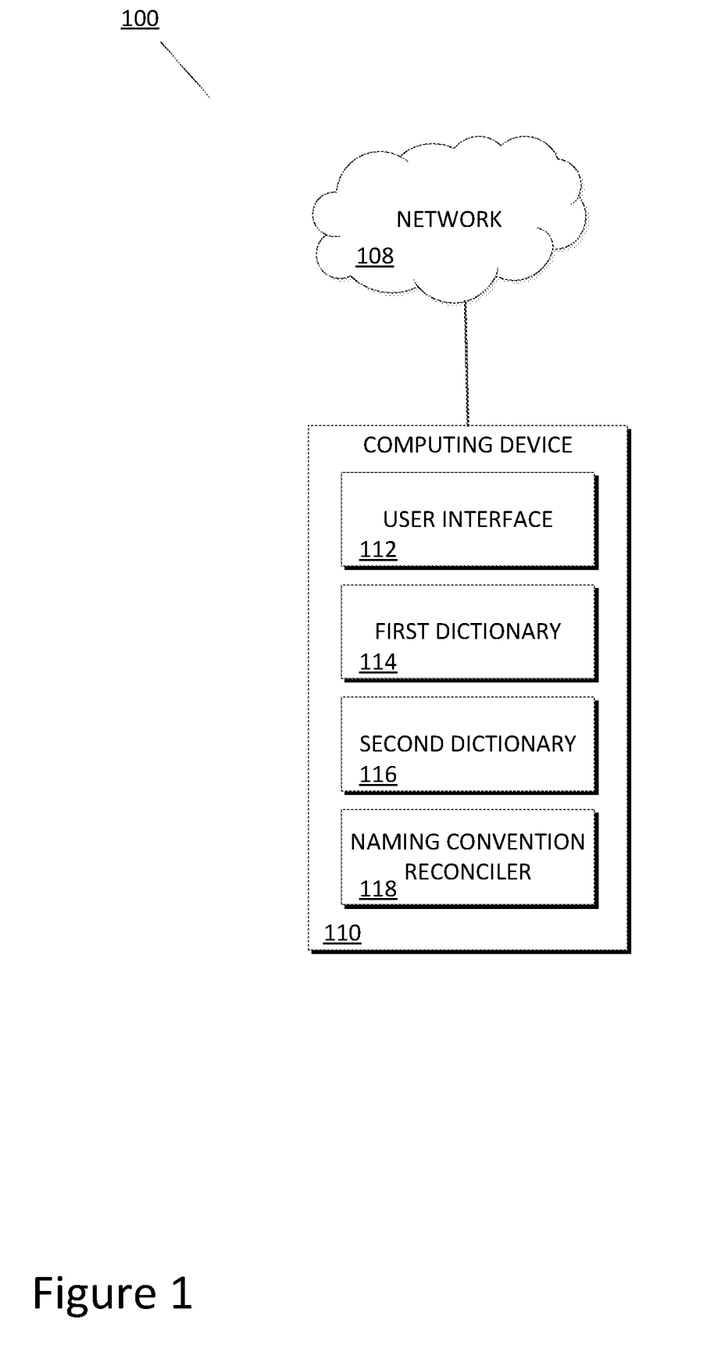
FIG. 1 is a schematic diagram of naming convention reconciling system 100, in accordance with an embodiment of the present invention.

A naming convention reconciling system 100, in accordance with an embodiment of the invention, is illustrated by FIG. 1. In the example embodiment, naming convention reconciling system 100 includes network 108 and computing device 110.

In the example embodiment, network 108 is a communication channel capable of transferring data between connected devices. In the example embodiment, network 108 may be the Internet, representing a worldwide collection of networks and gateways to support communications between devices connected to the Internet. Moreover, network 108 may include, for example, wired, wireless, or fiber optic connections which may be implemented as an intranet network, a local area network (LAN), a wide area network (WAN), or any combination thereof. In further embodiments, network 108 may be a Bluetooth network, a WiFi network, or a combination thereof. In yet further embodiments, network 108 may be a telecommunications network used to facilitate telephone calls between two or more parties comprising a landline network, a wireless network, a closed network, a satellite network, or any combination thereof. In general, network 108 can be any combination of connections and protocols that will support communications between computing device devices.

In the example embodiment, computing device 110 includes user interface 112, first dictionary 114, second dictionary 116, and naming convention reconciler 118. Computing device 110 may be a laptop computer, a notebook, a tablet computer, a netbook computer, a personal computer (PC), a desktop computer, a personal digital assistant (PDA), a smart phone, a mobile phone, a virtual device, a thin client, a server, or any other electronic device or computing system capable of receiving and sending data to and from other computing devices. While computing device 110 is shown as a single device, in other embodiments, computing device 110 may be comprised of a cluster or plurality of computing devices, working together or working separately. Computing device 110 is described in more detail with reference to FIG. 5.

User interface 112 is a software application that allows a user of computing device 110 to interact with computing device 110 as well as other connected devices via network 108. User interface 112 may be connectively coupled to hardware components, such as those depicted by FIG. 5, for receiving user input, including mice, keyboards, touchscreens, microphones, cameras, and the like. In the example embodiment, user interface 112 is implemented via a standalone application that includes a graphical user interface (GUI) that is capable of transferring data files, folders, audio, video, hyperlinks, compressed data, and other forms of data transfer individually or in bulk. In other embodiments, user interface 112 may be implemented via other integrated or standalone software applications and hardware capable of receiving user interaction and communicating with other electronic devices.

First dictionary 114 is a file containing a list of one or more names corresponding to one or more things named in accordance with a particular naming convention. In the example embodiment, first dictionary 114 lists disease names named in accordance with a first naming convention, for example a proprietary company naming convention. Files comprising first dictionary 114 may be written in programming languages of common file formats such as .txt, .csv, .docx, .doc, .rtf, .xls, .pdf, etc. While in the example embodiment first dictionary 114 is stored locally on computing device 110, in other embodiments, first dictionary 114 may be stored remotely and accessed via network 108. In such embodiments, first dictionary 114 may be stored on a computing device or any suitable form of storage medium. First dictionary 114 is described in greater detail with respect to FIGS. 2-4.

Second dictionary 116 is a file containing a list of one or more names corresponding to one or more things named in accordance with a particular naming convention. In the example embodiment, second dictionary 116 lists disease names named in accordance with a second naming convention, for example the Disease Ontology naming convention. Files comprising second dictionary 116 may be written in programming languages of common file formats such as .txt, .csv, .docx, .doc, .rtf, .xls, .pdf, etc. While in the example embodiment second dictionary 116 is stored locally on computing device 110, in other embodiments, second dictionary 116 may be stored remotely and accessed via network 108. In such embodiments, second dictionary 116 may be stored on a computing device or any suitable form of storage medium. Second dictionary 116 is described in greater detail with respect to FIGS. 2-4.

In the example embodiment, naming convention reconciler 118 is a software application capable of receiving and pre-processing first dictionary 114 and second dictionary 116. In addition, naming convention reconciler 118 is capable of parsing the pre-processed dictionaries to extract one or more names from each of the two dictionaries. Moreover, naming convention reconciler 118 is further capable of creating a hash table of the names extracted from the second dictionary and searching the hash table for names that include a word in common with a name extracted from first dictionary 114. Based on identifying a name in the hash table that includes a word in common with a name extracted from first dictionary 114, naming convention reconciler 118 is capable of determining a similarity between the names and storing an association between the names having a greatest similarity. The operations of naming convention reconciler 118 are described in greater detail with respect to FIGS. 2-4, below.

Figure 2:
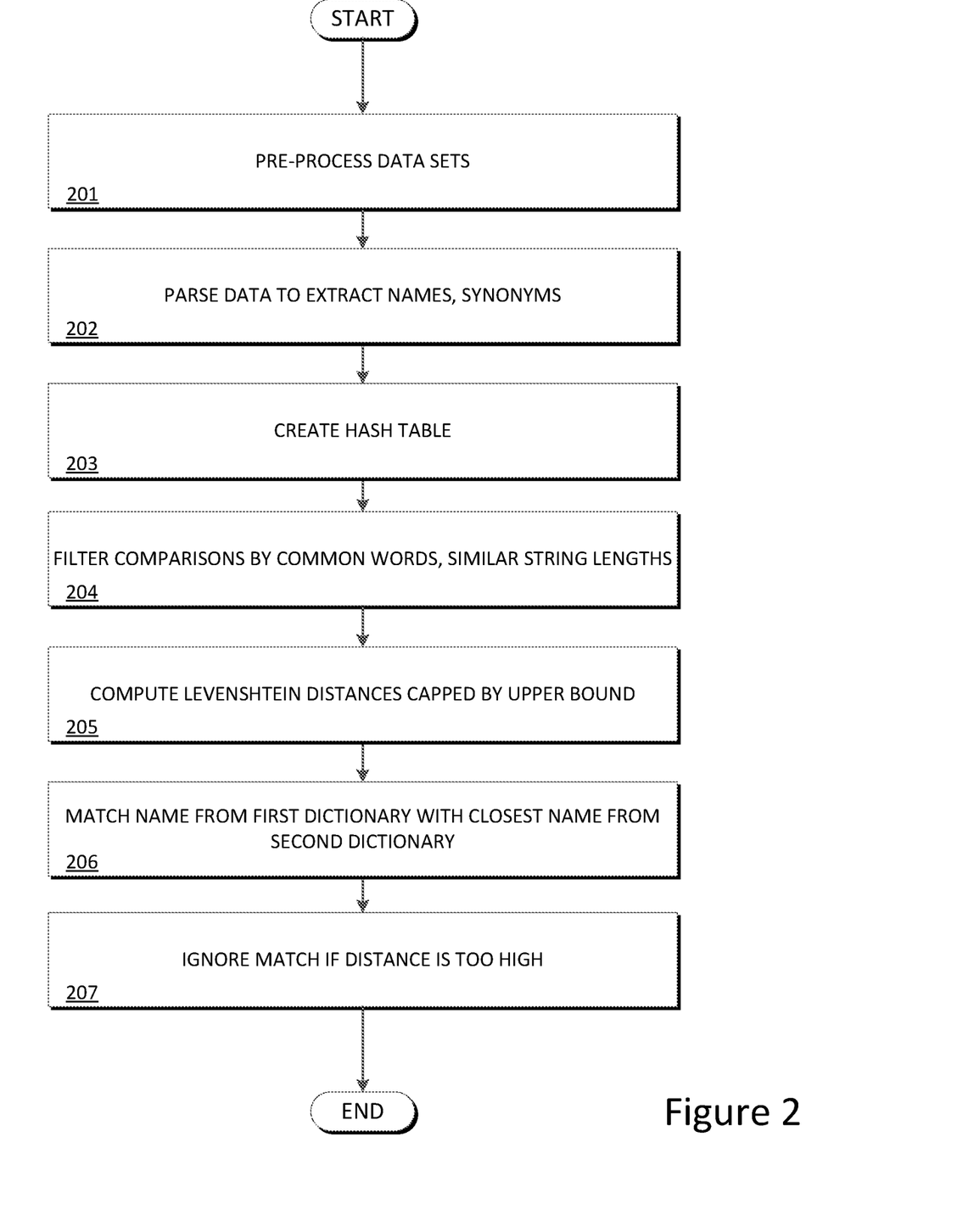
FIG. 2 depicts a schematic diagram illustrating the operations of naming convention reconciler 118 of naming convention reconciling system 100, in accordance with an embodiment of the present invention.

FIG. 2 illustrates the operations of naming convention reconciler 118 of naming convention reconciling system 100 in accordance with an embodiment of the present invention. In the example embodiment, naming convention reconciler 118 identifies and converts (translates, reconciles, etc.) synonymous names across different naming conventions in order to increase nomenclature consistency amongst data within a same domain. Such identifications are then stored, based on user preferences, such that future analytics take into account both naming convention names. The proceeding detailed description, in combination with FIGS. 2-4, describes this process in more detail.

In many fields, there are multiple naming conventions. For example, in the biomedical field, there are multiple ways to name diseases. These include Unified Medical Language System (UMLS) Concept Unique Identifiers (CUI), Online Mendelian Inheritance in Man (OMIM), Disease Ontology, International Classification of Diseases (ICD-9), Systemized Nomenclature of Medicine (SNOMED) clinical terms, National Cancer Institute (NCI) Disease Codes, and others. Even some companies have their own proprietary disease naming conventions. There is often a need to translate names in one convention (e.g. a proprietary disease naming convention) to another (e.g. Disease Ontology, UMLS CUIs, others). This invention addresses this need.

This invention is broadly applicable to translating names between different naming conventions in a broad range of disciplines. While the illustrated embodiments are described with respect to translation between different disease naming conventions, it is applicable to many other domains outside of the disease and biomedical areas as well.

FIG. 2 depicts a flowchart illustrating the conversion of names between different naming conventions in accordance with the present invention. In the example embodiment, disease names from a proprietary disease-naming convention developed by a company are converted by naming convention reconciler 118 to the Disease Ontology disease-naming convention. Note that this invention can be used for converting names to different naming conventions for a lot of other domains as well.

The proprietary and the Disease Ontology disease naming conventions are initially contained in first dictionary 114 and second dictionary 116, respectively. In Step 201, the data in these files are ingested and converted to a format compatible with naming convention reconciler 118. In Step 202, the data are parsed to extract disease names. The proprietary disease naming convention data also contains disease synonyms (explained later) which are extracted.

Since the number of names in a disease-naming convention can be large, it can be inefficient to compare each name in one disease-naming convention to each name in another disease-naming convention to see if they are a good match. We thus employ techniques to reduce the number of comparisons that are made. One technique which can be used is to compare names if they have a word in common but otherwise not compare the names. Another technique is to compare names if they are close in length but not compare them if their lengths differ by too much. In FIG. 2, both of these techniques are used. In other embodiments of the invention, only one or none of these techniques may be employed.

Step 203 is useful for determining names which have at least one word in common. A hash table indexed by words in Disease Ontology names, i.e. second dictionary 116, is maintained. Nonempty buckets in the hash table contain a list of Disease Ontology IDs corresponding to the Disease Ontology names containing the word indexing the hash bucket. For example, Disease Ontology ID "DOID: 0050032" refers to "mineral metabolism disease". "DOID: 0050032" would be stored (as list elements) in the hash table buckets corresponding to the words "mineral", "metabolism", and "disease".

In Step 204, the number of comparisons that need to be made is restricted to improve the efficiency of the algorithm. One of the techniques is to restrict comparisons to disease names with at least one word in common. For example, consider the company disease name "2-vessel coronary artery stenosis". We can find Disease Ontology names which contain the word "coronary" by looking up "coronary" in the hash table.

We can also restrict the number of comparisons by only comparing disease names if their lengths are similar. For example, the following approaches can be used to determine whether to compare two names n1 and n2:

Only compare n1 and n2 if the quotient of their length is close to 1. For example, only compare n1 and n2 if the quotient of their length is between 1−t1 and 1+t1 for a threshold value t1.

Only compare n1 and n2 if the difference between their lengths is less than a threshold.

Some other approach which restricts comparisons unless the lengths of n1 and n2 are similar.

If a proprietary disease name and one or more Disease Ontology names pass the filtering Step 204, the proprietary disease name is compared to one or more Disease Ontology names in Step 205. Levenshtein Distances (described in greater detail with respect to FIG. 4) are a suitable method used for the comparisons. However, the invention can use other methods besides Levenshtein distances for comparing names, including, but not limited to, some of the methods described with respect to FIG. 4.

When calculating a Levenshtein distance between 2 names, we specify an upper bound on the distance between the names, u1. If the Levenshtein distance between the names exceeds u1, the names are considered too dissimilar to constitute a match. u1 can be passed as a parameter to the method that calculates Levenshtein distances. Once this method determines that the Levenshtein distance between the names will exceed u1, it can terminate the calculation prematurely before determining the exact Levenshtein distance. This is more efficient than continuing the calculation to completion.

If there are multiple possible Disease Ontology names which might match a proprietary disease name that pass filtering Step 204, a Disease Ontology name which results in a least Levenshtein Distance is considered to be the correct translation for the proprietary disease name, provided the Levenshtein distance does not exceed u1 (Steps 206 and 207).

A proprietary disease name may comprise one or more synonyms wherein multiple synonyms refer to the same disease. For example, "abnormality of aortic valve cusp prolapse left coronary" and "prolapse of left coronary aortic valve cusp" are synonyms referring to the same disease.

For simplicity, the above description is for a situation when a proprietary disease name comprises a single synonym.

If there are a plurality of synonyms, then the above matching process can be applied to multiple synonyms. If at least one synonym has a match with a Disease Ontology name that passes filtering Step 204, then a Disease Ontology name which results in a least Levenshtein Distance across all synonyms is considered to be a correct translation for the proprietary disease name.

If an exact match is found between a proprietary disease name and a Disease Ontology name, it is not necessary to continue making comparisons between the disease name and other Disease Ontology names or between a different synonym for the proprietary disease name and any Disease Ontology names.

Figure 3:
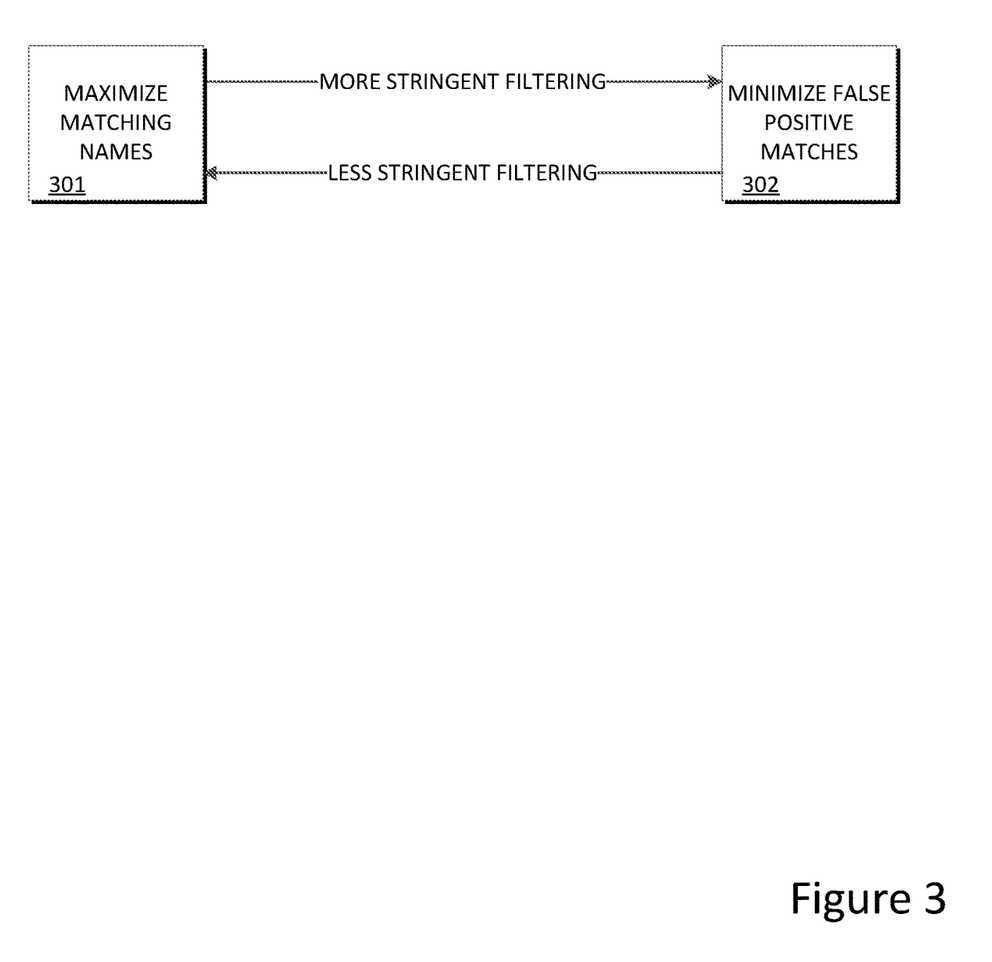
FIG. 3 depicts a schematic diagram illustrating the effect of more and less stringent filtering, in accordance with an embodiment of the present invention.

The upper bound on the distance between names, u1, can be used to achieve a balance between finding a large number of name translations and making precise name translations (FIG. 3). If u1 is high, then the algorithm will make a high number of disease translations (301). The drawback is that the algorithm is prone to translating disease names incorrectly. If u1 is low, then the algorithm will make fewer incorrect name translations (302). The drawback is that fewer names will be translated.

The value of u1 can be adjusted appropriately to achieve an optimal balance between finding a large number of name translations and translating names correctly. It may be desirable to run the algorithm with different values of u1 to determine which value(s) work best. It may also be valuable to use translations resulting from multiple values of u1.

Figure 4:
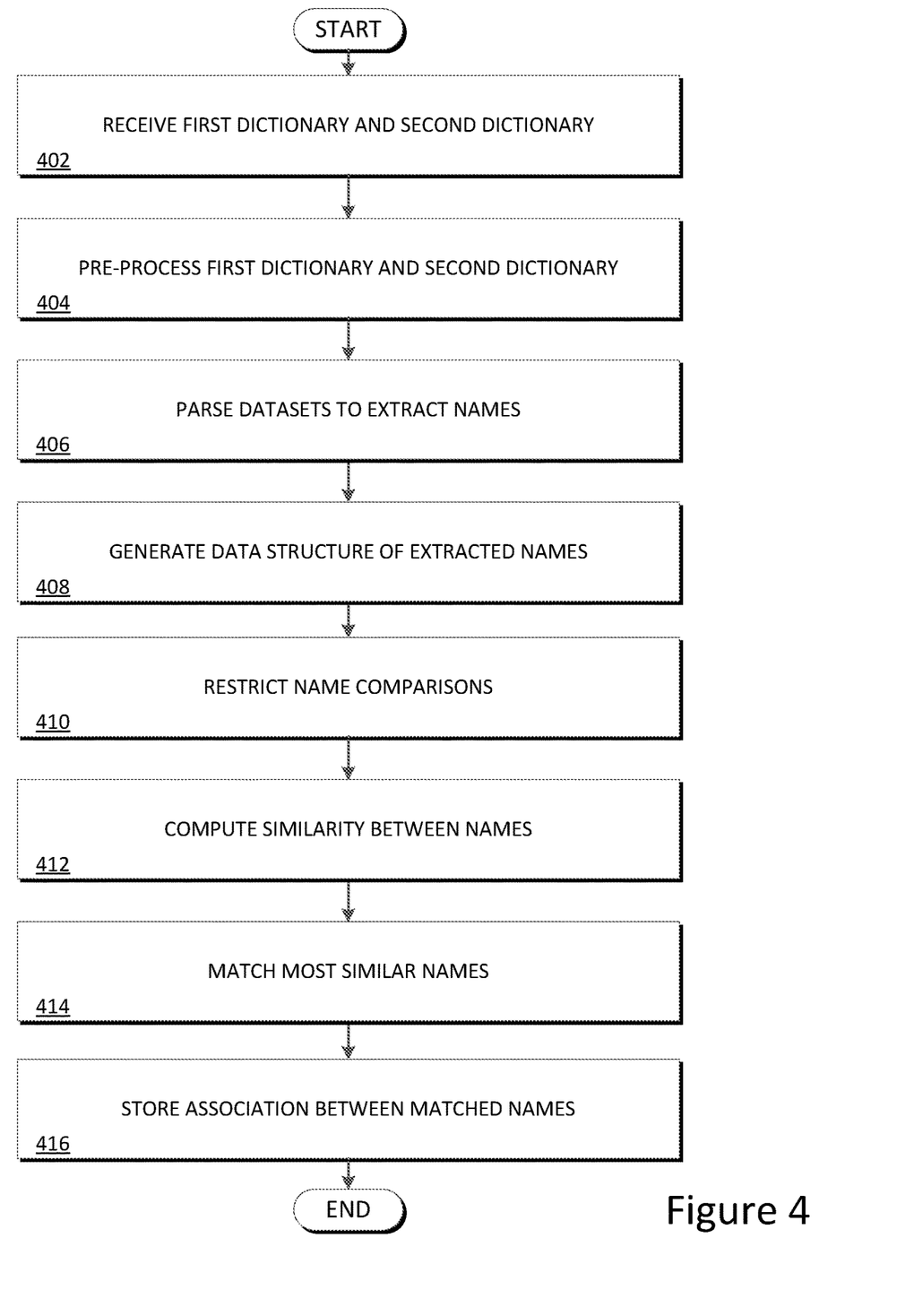
FIG. 4 depicts a schematic diagram illustrating the operations of naming convention reconciler 118 of naming convention reconciling system 100, in accordance with an embodiment of the present invention.

FIG. 4 illustrates an alternative embodiment of the operations of naming convention reconciler 118.

Naming convention reconciler 118 receives first dictionary 114 and second dictionary 116 (step 402). While in the example embodiment, first dictionary 114 and second dictionary 116 are stored locally, in other embodiments, first dictionary 114 and second dictionary 116 may be stored remotely and accessed via network 108. Moreover, data stored in first dictionary 114 and second dictionary 116 are named in accordance with different naming conventions and therefore a same thing, entity, idea, concept, etc. present in both datasets may be stored under a different name in first dictionary 114 than in the second dictionary 116. In some embodiments, each respective dictionary may detail large amounts of data that regard a variety of domains while, in other embodiments, each dataset may detail a particular domain, such as the medical, financial, and legal fields. In some embodiments, the dictionaries may simply comprise a list of names or strings. In any use of the present invention, however, both first dictionary 114 and second dictionary 116 contain at least some data regarding a same thing, entity, concept, etc.

In the former case where each dictionary contains data from a variety of domains (step 402 continued), naming convention reconciler 118 may additionally receive a desired domain from the user via user interface 112 to limit analysis to a particular field or discipline. In such embodiments, the domain acts to restrict the analysis to a particular field in order to increase both efficiency and accuracy in identifying synonymous names within a variety of naming conventions. That is, by limiting the analysis to names of a particular domain, naming convention reconciler 118 avoids analysing names that may appear to be related yet have no relation to one another, thereby increasing computational efficiency. Moreover, restricting the analysis to a particular domain increases accuracy of the results by reducing a likelihood of misinterpretation, such as misinterpreting unrelated homonyms that are present in two or more unrelated domains. In the latter case where the received dictionaries are specific to a particular domain, a user may omit the step of entering a domain because the data is already limited to a particular field.

In other embodiments (step 402 continued), naming convention reconciler 118 may be configured to identify and upload datasets without the need for user input or interaction. For example, naming convention reconciler 118 may be configured to receive a desired domain and search large amounts of data, for example entire databases, for two or more dictionaries that detail the received domain, yet implement different naming conventions. Alternatively, naming convention reconciler 118 may be configured to receive a database and identify two or more dictionaries within the database that detail a same domain but implement different naming conventions. In such embodiments, naming convention reconciler 132 may identify domains using techniques such as natural language processing in combination with resources such as relational databases.

Naming convention reconciler 118 pre-processes the received first dictionary 114 and second dictionary 116 (step 404). In the example embodiment, naming convention reconciler 118 pre-processes first dictionary 114 and second dictionary 116 by first ingesting the file(s) which comprise the dictionaries and converting them to a format compatible with naming convention reconciler 118. In some embodiments, pre-processing may also include techniques to reduce irrelevance, redundancy, noise, and unreliability of the dictionaries that result from data imperfections such as out-of-range values, impossible data combinations, missing values, and the like. When needed, pre-processing converts and, in some embodiments, increases a quality of the dictionaries such that naming convention reconciler 118 can later perform more effective and efficient knowledge discovery. In the example embodiment, naming convention reconciler 118 pre-processes the dictionaries using methods such as data conversion, data cleansing, data editing, data reduction, data wrangling, cleaning, instance selection, normalization, transformation, feature extraction, and feature selection. Moreover, in some embodiments, naming convention reconciler 118 may pre-process the dictionaries in consideration of the received domain such that pre-processing results in greater quality dictionary for later analysis. For example, naming convention reconciler 118 may refine an understanding of out-of range values and impossible combinations in light of the selected domain.

Naming convention reconciler 118 parses first dictionary 114 and second dictionary 116 to extract one or more names from each of the respective dictionaries (step 406). In the example embodiment, one or more names are extracted from first dictionary 114 and one or more names are extracted from second dictionary 116. Each name extracted from first dictionary 114 is a candidate synonym for an extracted name from second dictionary 116, and vice versa, as will be described with greater detail below. To parse the dictionaries, naming convention reconciler 118 utilizes parsing techniques, such as generating a parse tree, that decompose names within the files into their constituent parts to show a syntactic and semantic relations to each other. Naming convention reconciler 118 then cross-references the resulting constituents names with information resources, such as a domain-specific relational database, in order to identify a list of names, as well as synonyms thereof, from each dictionary that correspond to the identified domain. The resulting, extracted names from each respective dictionary are later compared to one another to determine whether any are synonymous. While in the example embodiment the dictionaries are parsed in light of the received or deduced domain, in other embodiments, the dictionaries may be generically parsed.

Naming convention reconciler 118 generates a data structure corresponding to the extracted names (step 408). Because the number of names corresponding to a naming convention can be very large, it can be inefficient to compare each name in one dictionary to each name in another dictionary to see if they are a good match, e.g. compare all names extracted from first dictionary 114 to all names extracted from second dictionary 116. The invention herein thus employ techniques to reduce the number of comparisons that are made. For example, one technique utilized by naming convention reconciler 118 is to only compare names that have a word or threshold series of consecutive characters in common. Alternatively, or in combination, naming convention reconciler 118 may implement a technique wherein names are only compared if they are close in character length.

In order to apply these techniques efficiently (step 408 continued), naming convention reconciler 118 first creates a data structure of at least one of the dictionaries. In the example embodiment, for instance, naming convention reconciler 118 creates a hash table of the names extracted from second dictionary 116. Generating a hash table is a technique that improves data storage and retrieval by implementing an associative array abstract data type that maps keys to values using a hash function. While the example embodiment implements a hash table data structure, other embodiments may generate alternative data structures, such as arrays, linked lists, records, unions, tagged unions, and classes. Moreover, in these other embodiments, naming convention reconciler 118 may additionally generate a data structure of the names extracted from first dictionary 114.

Naming convention reconciler 118 restricts name comparisons (step 410). As described above with reference to the generation of the data structure, naming convention reconciler 118 restricts name comparisons in order to remove names which are unlikely to be synonymous with each other, thereby increasing computational efficiency. In the example embodiment, naming convention reconciler 118 restricts name comparisons using several constraints. For example, naming convention reconciler 118 may be configured to only compare names having a word in common or to only compare names that are similar in length. In the example embodiment, naming convention reconciler 118 restricts the comparisons based on names having a word in common using the hash table. More specifically, naming convention reconciler 118 will search the hash table that comprises names extracted from second dictionary 116 for words in a name extracted from first dictionary 114. Naming convention reconciler 118 then restricts comparisons in the next step to those names having a word in common. While in the example embodiment, naming convention reconciler 118 restricts based on names, other embodiments may implement restrictions based on series of consecutive characters, or spans. In addition, naming convention reconciler 118 may restrict comparisons by determining whether the names share a similar length, for example determining whether one name (n1) has within a threshold amount of characters of the other name (n2) (i.e. n1-n2>|5|). In another example, naming convention reconciler 118 may restrict comparison to names where the quotient of one name length (n1) divided by the other name length (n2) is within a tolerance of one (i.e. n1/n2=1±0.1). Naming convention reconciler 118 then only compares names having said similar length. While only several restricting techniques are described above, it will be appreciated that many other restricting techniques based on syntactic similarity may be employed in the present invention.

In addition (step 410 continued), naming convention reconciler 118 may be further configured to perform filtering based on semantic and/or pragmatic analysis and, for example, may filter based on parts of speech, language-independent meaning, linguistic and/or cultural context, idioms/figurative speech, and other language characteristics. For example, and based in part on the parsing performed earlier, naming convention reconciler 118 may identify a part of speech corresponding to a name and only compare it to names having a same part of speech. In addition, naming convention reconciler 118 may further analyse several words within a proximity of the name in order to deduce a context, meaning, or intent of the name based on natural language processing. Naming convention reconciler 118 may then repeat the process for the other name and restrict comparisons to names whose use match the context, meaning, or intent of the other name. In the example embodiment, such semantic and pragmatic analyses may include techniques such as latent semantic analysis, latent dirichlet allocation, generating vector models, and generating hidden Markov Models. In other embodiments, however, other semantic and pragmatic analysis techniques may be implemented. In general, any filtering technique or combination of filtering techniques, whether they be syntactic, semantic, pragmatic, or otherwise may be implemented in accordance with the invention herein in order to reduce resource consumption or otherwise improve naming convention reconciler 118.

Naming convention reconciler 118 computes a similarity between the names (step 412). In the example embodiment, naming convention reconciler 118 computes a similarity between the restricted names using one or more string similarity metrics that may be syntactic, semantic, pragmatic, etc., or a combination thereof. In the example embodiment, for instance, naming convention reconciler 118 utilizes a Levenshtein distance where similarity is based on an amount of additions, deletions, and substitutions needed to convert one name to another. For example, the Levenshtein distance between "for" and "four" is one because one character, namely "u", must be added to convert the former to the latter. In other embodiments, however, naming convention reconciler 118 may implement other metrics such as a Damerau-Levenshtein distance, an edit distance, a Hamming distance, inversion, a Jaccard index, a Jaro-Winkler distance, a Lee distance, most frequent k characters, a Needleman-Wunsch algorithm, an overlap coefficient, a simple matching coefficient, a Sorensen-Dice coefficient, string kernel, a Tversky index, and a Wager-Fischer algorithm.

In the example embodiment, where similarity is calculated based on a distance metric, naming convention reconciler 118 may be further configured to apply an upper bound, u1, in determining the distances such that once the upper bound distance between names is reached, naming convention reconciler 132 prematurely terminates the similarity calculation before determining the exact distance in order to conserve resources. In the example embodiment, the upper bound may be adjusted to achieve a balance between reconciling a large number of names and making precise reconciliations based on user preferences. For example, if the upper bound is set high, as depicted by FIG. 3, naming convention reconciler 132 will calculate similarities for and reconcile many names, however will be more prone to reconciling names incorrectly. Conversely, if the upper bound is low, then naming convention reconciler 118 will make be less prone to incorrectly reconciling names, however will reconcile less of the names. This balance may be adjusted accordingly by a user to achieve a desired balance in consideration of a granularity of the domain, processing power, and the like. In some embodiments, iterations of the process may be performed using different upper bounds and the results may be weighted and compiled. In general, it will be appreciated that many different scoring and ranking algorithms may be implemented in the embodiments of the present invention suitable for calculating a similarity between names.

Naming convention reconciler 118 matches the names having a greatest similarity (step 414). In the example embodiment, naming convention reconciler 118 matches names based on a similarity of the names calculated in a previous step. If, for example, there is an exact match between two names (e.g. Levenshtein distance=0), then naming convention reconciler 118 considers the names a correct match. Otherwise, naming convention reconciler 118 is configured to match names having a greatest similarity. For example, in embodiment utilizing string metrics involving distances, naming convention reconciler 118 will match names having a lowest calculated distance. In embodiments implementing semantic and/or pragmatic analysis, naming convention reconciler 118 may match names having a highest probability, or confidence, of being synonymous. In further embodiments, a hybrid analysis combining syntactic, semantic, pragmatic, or heuristic analysis may be implemented to identify a most likely matching name. In cases of tie, e.g. a name in one convention has a same similarity to two names in another convention, naming convention reconciler 118 may be configured to prompt user interaction for selection of an appropriate name. Alternatively, naming convention reconciler 118 may be configured to reference other resources to determine which of the two names has a greater relation to the corresponding name or domain.

Naming convention reconciler 118 stores an association between the names having a greatest similarity (step 416). In some embodiments, such an association may be automatically performed and warranted when in certain circumstances while, in others, the storing of the association may be triggered by specific events. For example, if the names are an exact match, then naming convention reconciler 118 may be configured to automatically store the association. In other embodiments where the names are not an exact match, naming convention 142 may be configured to generate a confidence level based on the similarity determined above and automatically store the name association when the confidence level exceeds a particular threshold. In other embodiments, or when the confidence level is less than that of the particular threshold, naming convention reconciler 118 may prompt a user, via user interface 112, to confirm the matched association prior to storage. In addition, naming convention reconciler 118 may be further configured to receive input further specifying whether the matched names include a parent, class, or subclass of the other.

While the present invention has been described and illustrated with reference to particular embodiments, it will be appreciated by those of ordinary skill in the art that the invention lends itself to many different variations not specifically illustrated herein.

The present invention may be a system, a method, and/or a computer program product. The computer program product may include a computer readable storage medium (or media) having computer readable program instructions thereon for causing a processor to carry out aspects of the present invention.

Figure 5:
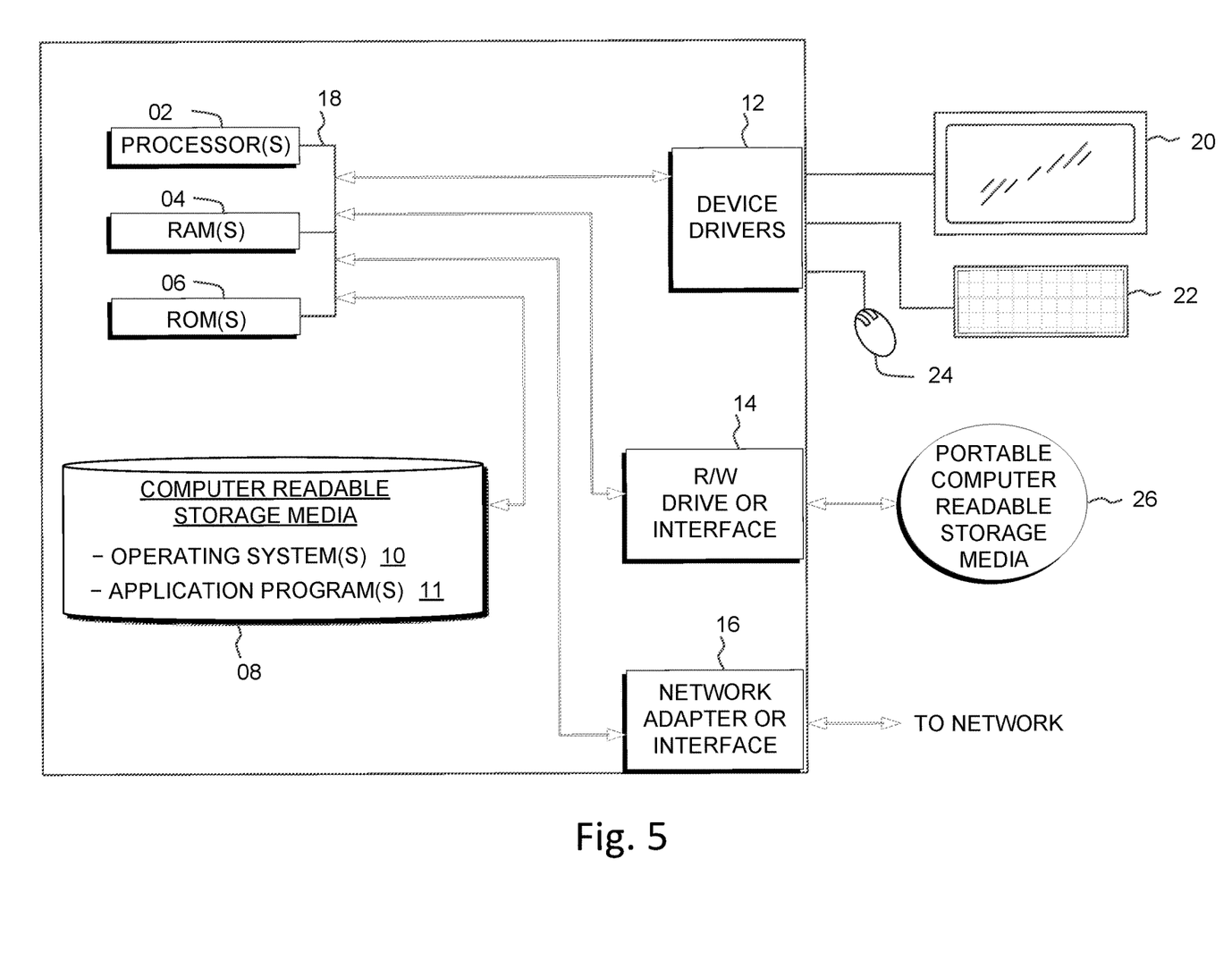
FIG. 5 is a block diagram depicting the hardware components of naming convention reconciling system 100 of FIG. 1, in accordance with an embodiment of the invention.

FIG. 5 depicts a block diagram of components of computing device 110 of naming convention reconciling system 100 of FIG. 1, in accordance with an embodiment of the present invention. It should be appreciated that FIG. 5 provides only an illustration of one implementation and does not imply any limitations with regard to the environments in which different embodiments may be implemented. Many modifications to the depicted environment may be made.

Computing device 110 may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11, for example naming convention reconciler 118, are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Computing device 110 may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Computing device 110 may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Computing device 110 may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
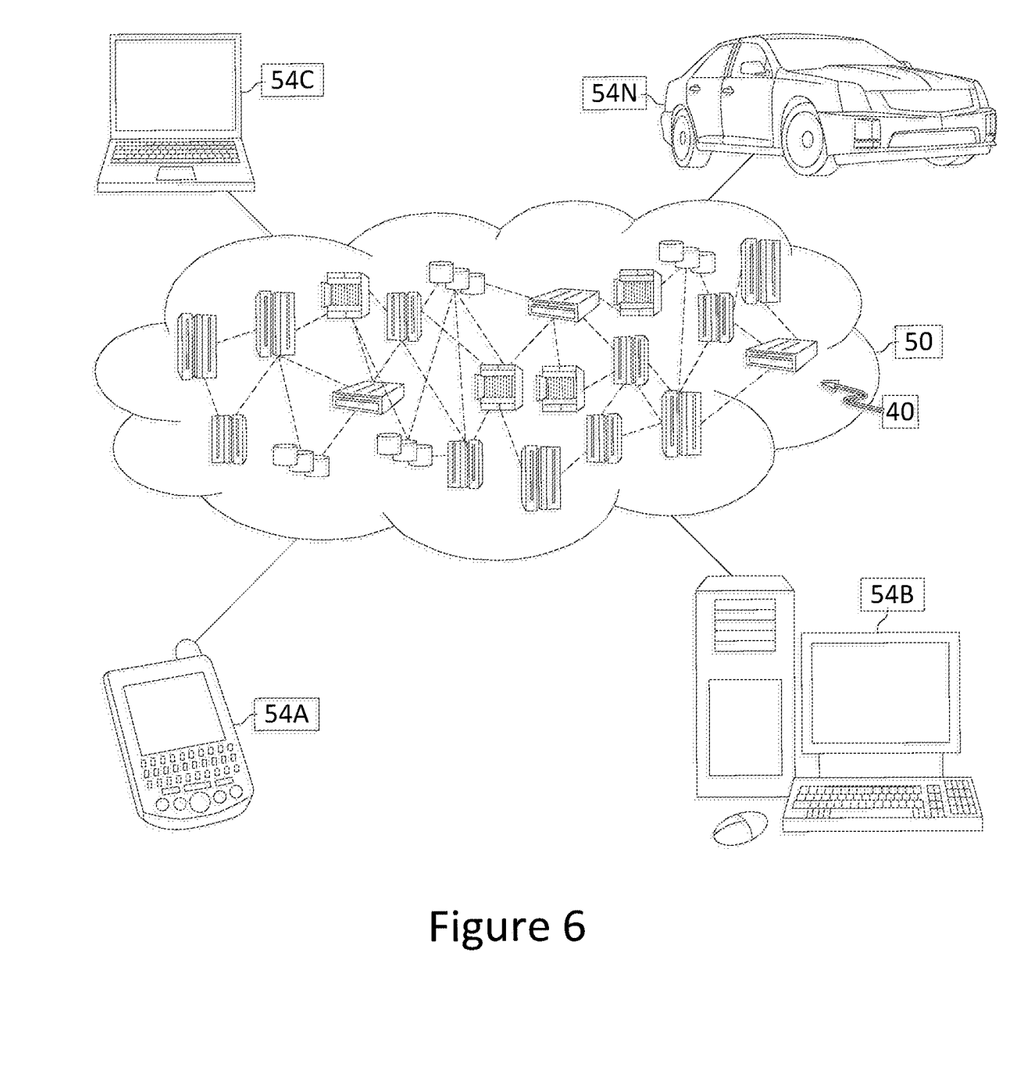
FIG. 6 depicts a cloud computing environment, in accordance with an embodiment of the present invention.

Referring now to FIG. 6, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 40 and cloud computing environment 50 can communicate with any type of computerized device over any type of network and/or network addressable connection (e.g., using a web browser).

Figure 7:
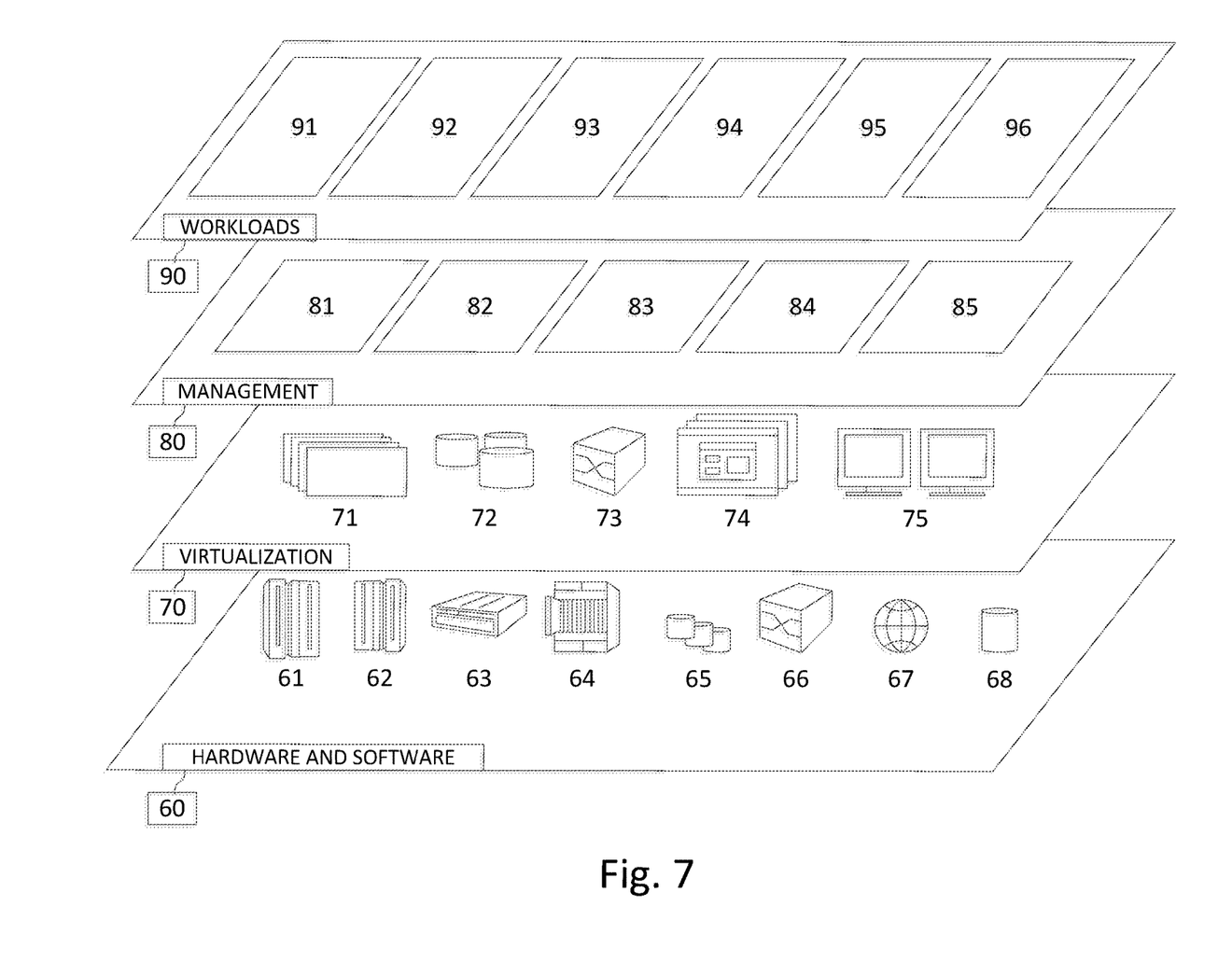
FIG. 7 depicts abstraction model layers, in accordance with an embodiment of the present invention.

Referring now to FIG. 7, a set of functional abstraction layers provided by cloud computing environment 50 (FIG. 4) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and name processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer implemented method for increasing computational efficiency of a computer to convert a name n1 from a first naming convention to a second naming convention, comprising:
   searching for one or more names from the second naming convention having a word in common with name n1 and generating a data structure corresponding to the one or more names;
   in response to finding the one or more names from the second naming convention having the word in common with the name n1, using a metric to determine a difference between the name n1 and the one or more names; and
   selecting, using the data structure, a name n2 of the one or more names having the word in common with the name n1 and a fewest difference from the name n1;
   wherein searching for at least one name from the second naming convention having a word in common with name n1 further comprises:
   maintaining a hash table indexed by words, wherein a hash bucket of the hash table includes a list of identifiers of names in the second naming convention which include a word indexing the bucket of the hash table; and
   searching the hash table for data associated with a word included in name n1.

2. The method of claim 1, wherein the metric comprises Levenshtein distances.

3. The method of claim 1, further comprising:
using a metric to determine differences between name n1 and a plurality of names from the second naming convention having a word in common with name n1; and
selecting a name from the plurality of names from the second naming convention having a word in common with name n1 with a lowest difference from name n1.

4. The method of claim 1, further comprising:
decreasing a threshold to obtain more precise conversions between the first naming convention and the second naming convention.

5. The method of claim 1, further comprising:
increasing a threshold to obtain more conversions between the first naming convention and the second naming convention.

6. A computer program product increasing computational efficiency of a computer to convert a name n1 from a first naming convention to a second naming convention, the computer program product comprising:
one or more computer-readable storage devices and program instructions stored on at least one of the one or more tangible storage devices, the program instructions comprising:
program instructions to search for one or more names from the second naming convention having a word in common with name n1;
program instructions to generate a data structure corresponding to the one or more names;
in response to finding the one or more names from the second naming convention having the word in common with the name n1, program instructions to use a metric to determine a difference between the name n1 and the one or more names; and
program instructions to select a name n2 of the one or more names having the word in common with the name n1 and a fewest difference from the name n1;
wherein searching for at least one name from the second naming convention having a word in common with name n1 further comprises:
program instructions to maintain a hash table indexed by words, wherein a hash bucket of the hash table includes a list of identifiers of names in the second naming convention which include a word indexing the bucket of the hash table; and
program instructions to search the hash table for data associated with a word included in name n1.

7. The computer program product of claim 6, wherein the metric comprises Levenshtein distances.

8. The computer program product of claim 6, further comprising:
program instructions to use a metric to determine differences between name n1 and a plurality of names from the second naming convention having a word in common with name n1; and
program instructions to select a name from the plurality of names from the second naming convention having a word in common with name n1 with a minimum difference from name n1.

9. The computer program product of claim 6, further comprising:
program instructions to decrease said threshold to obtain more precise conversions between the first naming convention and the second naming convention.

10. The computer program product of claim 6, further comprising:
program instructions to increase said threshold to obtain more conversions between the first naming convention and the second naming convention.

11. A method, in a data processing system comprising at least one processor and at least one memory, the at least one memory comprising instructions executed by the at least one processor to cause the at least one processor to implement a method for increasing computational efficiency of a computer to convert a name n1 from a first naming convention to a second naming convention, the method comprising:
program instructions to search for one or more names from the second naming convention having a word in common with name n1;
program instructions to generate a data structure corresponding to the one or more names;
in response to finding the one or more names from the second naming convention having the word in common with the name n1, program instructions to use a metric to determine a difference between the name n1 and the one or more names; and
program instructions to select a name n2 of the one or more names having the word in common with the name n1 and a fewest difference from the name n1;
wherein searching for at least one name from the second naming convention having a word in common with name n1 further comprises:
program instructions to maintain a hash table indexed by words, wherein a hash bucket of the hash table includes a list of identifiers of names in the second naming convention which include a word indexing the bucket of the hash table; and
program instructions to search the hash table for data associated with a word included in name n1.

12. The computer system of claim 11, wherein name n1 and name n2 pass the filter if the difference in their lengths falls below a length threshold.

13. The computer system of claim 11, wherein the filter is based on a quotient of a length of name n1 and a length of name n2.

14. The computer system of claim 13 wherein name n1 and name n2 pass the filter if the quotient of a length of name n1 and a length of name n2 differs from 1 by less than a threshold.

15. The computer system of claim 11, wherein the metric comprises a Levenshtien distance.

16. The computer system of claim 11, further comprising:
program instructions to use a metric to determine differences between name n1 and a plurality of names from the second naming convention having a word in common with name n1; and
program instructions to select a name from the plurality of names from the second naming convention having a word in common with name n1 with a minimum difference from name n1.

17. The computer system of claim 11, further comprising one of:
program instructions to decrease said threshold to obtain more precise conversions between the first naming convention and the second naming convention; and
program instructions to increase said threshold to obtain more conversions between the first naming convention and the second naming convention.

* * * * *